United States Patent [19]

Semler et al.

[11] 4,340,746

[45] Jul. 20, 1982

[54] PROCESS FOR THE PREPARATION OF THIOCHLOROFORMATES

[75] Inventors: Günther Semler, Kelkheim; Georg Schaeffer, Hofheim am Taunus, both of Fed. Rep. of Germany

[73] Assignee: Hoechst Aktiengesellschaft, Frankfurt am Main, Fed. Rep. of Germany

[21] Appl. No.: 181,428

[22] Filed: Aug. 26, 1980

[30] Foreign Application Priority Data

Aug. 28, 1979 [DE] Fed. Rep. of Germany ....... 2934657

[51] Int. Cl.³ ................. C07C 153/11; C07D 333/10; C07D 307/38
[52] U.S. Cl. ................. 549/78; 260/455 R; 549/478; 549/479
[58] Field of Search ............. 260/455 R, 347.4, 347.2; 549/78

[56] References Cited

U.S. PATENT DOCUMENTS

| | | | |
|---|---|---|---|
| 3,277,143 | 10/1966 | Tilles | 260/455 R |
| 3,299,114 | 1/1967 | Tilles | 260/455 R |
| 3,766,236 | 10/1973 | Thaler | 260/455 R |

*Primary Examiner*—John M. Ford
*Assistant Examiner*—Robert C. Whittenbaugh
*Attorney, Agent, or Firm*—Curtis, Morris & Safford

[57] ABSTRACT

Thiochloroformates are prepared by reaction of mercaptans with phosgene in the presence of carboxylic acid amides and/or urea derivatives as catalysts in amounts smaller than hitherto known for this application. The amounts range from about 0.02 to 0.2 mol %, relative to the corresponding starting mercaptan. Despite the small amounts of catalyst the reaction proceeds as with the use of larger catalyst amounts; however, work-up is simplified and the product yields are increased in most cases.

9 Claims, No Drawings

PROCESS FOR THE PREPARATION OF THIOCHLOROFORMATES

Thiochloroformates are interesting intermediates and final products in numerous fields, especially for plant protection (fungicides, nematocides etc.)

Numerous methods are known for the preparation of thiochloroformates. One usual method is the reaction of mercaptans (whereby there are to be understood in this case quite generally organic SH compounds) with phosgene. This reaction, however, proceeds in satisfactory manner to give the intended thiochloroformates only when using defined catalysts having a specific action. Such a catalyst having a specific action is for example active charcoal (U.S. Pat. No. 3,039,537). The decisive disadvantage of this catalyst, however, resides in the fact that it adsorbs considerable amounts of the starting and final products. On removal of the catalyst by filtration, the phosgene adsorbed causes technological difficulties due to partial desorption. When using fixed bed reactors, on the other hand, the adsorbed mercaptan and the corresponding thiochloroformate likewise adsorbed cause serious problems on change of product, that is, when another thiochloroformate is to be prepared with the use of the same catalyst.

The difficulties involved in the use of active charcoal as catalyst are not overcome, either, by the special two-step operation mode disclosed in German Offenlegungsschriften Nos. 2,721,683 and 2,809,776.

On the other hand, these difficulties due above all to adsorption can be overcome by using catalysts having no, or an insignificant, adsorptive power; especially, carboxylic acid amides (U.S. Pat. No. 3,277,143) and tertiary amines (U.S. Pat. No. 3,299,114) are known as catalysts of this kind.

These catalysts, used in an amount of from 1 to about 10 mol %, relative to the starting mercaptan, give quite satisfactory thiochloroformate yields in some cases (up to about 90%), as does the active charcoal catalyst, but work-up of the reaction batches by distillation is impossible without previous removal of the catalyst (without such removal, decomposition reactions, discoloration of the distillate, sublimation of solids etc. result). The catalyst is removed by washing with water or aqueous hydrochloric acid, which causes hydrolysis of the thiochloroformates to a certain extent, so that yield and quality of the intended final product are adversely affected. Moreover, when carrying out the process on an industrial scale, removal of the catalyst by washing with water or aqueous hydrochloric acid causes additional expenditure increasing the cost of the process.

Because this synthesis method for thiochloroformates by reaction of mercaptans with phosgene, it is desirable and an object of the invention is to improve the known processes.

In accordance with the invention, this object was achieved in a surprising and simple manner by using a smaller amount of catalyst in the process according to U.S. Pat. No. 3,277,143, and by employing alternatively derivatives of urea (amides of carbonic acid) in addition to the carboxylic acid amides cited there as catalysts.

An aspect of this invention is therefore a process for the preparation of thiochloroformates by reaction of mercaptans with phosgene in the presence of at least one carboxylic acid amide and/or urea derivative as catalyst, which comprises using the catalyst in an amount of from about 0.02 to 0.2, preferably about 0.05 to about 0.1, mol %, relative to the starting mercaptan.

It is very surprising to observe that the reaction proceeds as smoothly with the use of these small catalyst amounts as with the larger amounts indicated in U.S. Pat. No. 3,277,143. For, according to this patent it was to be expected that catalyst amounts below about 2% (relative to the starting mercaptan) are not, or are insufficiency, effective, since, for economic reasons, amounts of catalyst and other substances larger than required normally are not employed. The likewise surprising consequence of the improvement in accordance with the invention resides in fact that the reaction batches can be worked up without preliminary removal of the catalyst by distillation, and that nevertheless qualitatively perfect products are obtained in high yields.

As starting mercaptans for the process of the invention, any organic mercapto compound having one or more SH groups in the molecule can be used. Suitable representatives are the mercaptans cited in U.S. Pat. Nos. 3,277,143 and 3,299,114, especially those of the formula

R—SH, in which R is alkyl, having preferably 1 to 18, especially 1 to 8, carbon atoms; cycloalkyl, having preferably 5 to 6, especially 6, carbon atoms; alkenyl, having preferably 3 to 8, especially 3 to 4, carbon atoms; aryl, preferably phenyl or naphthyl, especially phenyl; aralkyl, preferably benzyl; or a heterocyclic radical, preferably thienyl or furyl. The foregoing are also suitably substituted by one or more inert substituents or the SH group.

Inert substituents of these radicals R are, above all halogen, preferably F, Cl, Br, especially Cl
alkoxy, preferably $(C_1–C_4)$-alkoxy, especially methoxy
aryloxy, preferably phenoxy
carboalkoxy, preferably carbo-$(C_1–C_4)$-alkoxy, especially carbomethoxy.

Except in the case where R is alkyl, suitable inert substituents are alkyl radicals, preferably having from 1 to 4 carbon atoms, especially $CH_3$.

In the case where the radicals R are substituted also by one or more SH groups, corresponding bi- and polyvalent mercaptans are provided.

Especially preferred starting materials are ethylmercaptan, n-propylmercaptan, iso-propylmercaptan, tert. butylmercaptan, amylmercaptan, n-octylmercaptan, cyclohexylmercaptan, allylmercaptan, benzylmercaptan, thiophenol, o-, m- and p-thiokresol, o-, m- and p-chlorothiophenol, dichlorothiophenols, bromothiophenols, fluorothiophenols, methoxythiophenols, ethoxythiophenols, phenoxythiophenols, carbomethoxythiophenols, α-thionaphthol, β-thionaphthol, dithiohydroquinone.

Especially preferred starting mercaptans are $(C_1–C_8)$-alkylmercaptans, phenylmercaptan or tolylmercaptans.

Catalysts for the process of the invention are carboxylic acid amides such as are substantially described in U.S. Pat. No. 3,277,143, and substituted ureas. The catalysts correspond especially to the following formula

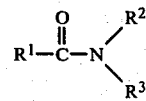

in which

R$^1$ is H, alkyl having preferably from 1 to 4 carbon atoms, phenyl or the group

R$^2$ and R$^3$, independently from each other, are H, alkyl, preferably having from 1 to 4 carbon atoms, phenyl, with the proviso that at least one of the radicals R$^1$, R$^2$ and R$^3$ is not H when R$^1$ is not

and at least one of the radicals R$^2$ and R$^3$ is not H when R$^1$ is

and two of the radicals R$^1$, R$^2$ and R$^3$ together, that is either R$^1$+R$^2$ or R$^3$, or R$^2$+R$^3$, may furthermore be alkylene, preferably having from 3 to 6 carbon atoms.

Examples of some distinct catalysts are the following:

dimethyl formamide
dimethyl acetamide
diethyl formamide
N,N-diethyl-propionic acid amide
benzoyl dimethylamine
tetramethyl urea
tetraethyl urea
tetra-n-butyl urea
N-methylpyrrolidone
N-acetylpiperidine
etc.

Especially preferred catalysts are dimethyl formamide, tetramethyl urea and N-methylpyrrolidone.

The cited catalysts can be used per se or in the form of practically any mixture with one another.

Alternatively, the catalysts may be used in the form of their reaction products with phosgene or the corresponding thiochloroformate (formed anyhow in the reaction); these reaction products, when starting from the mercaptans RSH, phosgene (CoCl$_2$), and catalysts

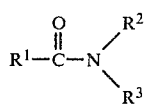

are mainly compounds of the formulae

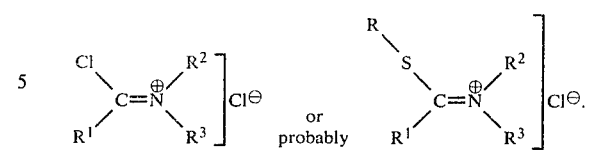

The details of operation conditions for the process of the invention are essentially those indicated in U.S. Pat. No. 3,277,143, that is, the reaction is generally carried out at room temperature or a temperature only slightly greater, because otherwise decomposition and side reactions occur or increase. The general temperature range is therefore from about 20° to 80° C., especially from 20° to 60° C.; in distinct cases of stable starting and final products, the temperature may be raised further.

The reaction is generally carried out under normal pressure; in special cases, however, elevated pressure is suitable.

Advantageously, operation is as follows: mercaptan and catalyst are introduced into the reactor, and phosgene in gaseous form is continuously passed through the reaction mixture. According to another embodiment, a mercaptan/catalyst mixture and phosgene are dosed in simultaneously, thus enabling continuous carrying out of the process.

When using starting mercaptans having a high melting point, operations may be carried out in the solvents usual for phosgenation reactions, for example chlorobenze, etc.

The reaction being complete, the excess dissolved phosgene is removed by purging with nitrogen, for example, and the batch is normally worked up by distillation. The yields of thiochloroformates are generally above those indicated in U.S. Pat. No. 3,277,143.

Due to the small amounts of catalyst and omission of one operation step (washing) in the work-up of the reaction product, the process in accordance with the invention provides an essential improvement of the known corresponding process, and therefore a considerable advancement of the art.

The following examples illustrate the invention.

EXAMPLE 1 n-Octylthiochloroformate

A mixture of 87.6 g of n-octylmercaptan and 0.09 g of N-methylpyrrolidone (15 mol %, relative to n-octylmercaptan) is introduced into a flask provided with stirrer, thermometer, phosgene inlet tube and a reflux condenser having an operational temperature of −20° C., and the mixture is treated at 50° C. with phosgene until in the gas chromatogram no starting product can be detected any more and/or until an increased phosgene reflux indicates that the reaction is complete. Stirring is continued for about 1 hour at 50° C., and then the excess phosgene and the remaining hydrogen chloride are blown off by means of nitrogen. The light yellow liquid obtained is distilled under reduced pressure (b.p. 85° C./1.3 mbar). 122.6 g (98% of theory) of a practically colorless n-octylthiochloroformate having a purity degree of 99% (GC analysis) are obtained.

COMPARATIVE EXAMPLE (LARGER AMOUNT OF CATALYST)

When the reaction as described in Example 1 is carried out with the use of 3 g of N-methylpyrrolidone (5 mol %, relative to n-octylmercaptan), only 94.0 g (75.1% of theory) of a deeply yellow n-octylthiochloroformate are obtained, the purity degree of which is 95% (GC).

EXAMPLES 2 to 7 WITH COMPARATIVE EXAMPLES

According to Example 1 and the corresponding Comparative Example, further Examples (2-7) and Comparative Examples were carried out; for details see the following Table. In this Table, the corresponding values from the Table in column 3 of U.S. Pat. No. 3,277,143 are listed, too (as far as existing).

TABLE

R—SH + COCl$_2$ → R—S—COCl + HCl

| Ex.: | R | Catalyst | Phosgenation Temperature (°C.) | Yield of thiochloroformate (% of th.) | Boiling point °C./mbar | Purity % | Color |
|---|---|---|---|---|---|---|---|
| 2 | n-C$_8$H$_{17}$— | 0.2 mol % DMF[1] | 50 | 98.0 | 85/1.3 | 99.0 | nearly colorless |
| Comp. | " | 3 mol % DMF[1] | 50 | 77.8 | | 97.0 | yellow |
| U.S.P. | " | 3 mol % DMF[1] | | 86 | | | |
| 3 | C$_2$H$_5$— | 0.1 mol % DMF[1] | 35-50 | 88.2 | 82/230 | 98.7 | light yellow |
| Comp. | " | 3 mol % DMF[1] | 35-50 | 75.3 | | 90.0 | deep yellow |
| U.S.P. | " | 3 mol % DMF[1] | | 79 | | | |
| 4 | n-C$_3$H$_7$— | 0.07 mol % TMH[2] | 50 | 93.2 | 67/40 | 98.7 | colorless |
| Comp. | " | 3 mol % TMH[2] | 50 | 91.0 | | 98.0 | nearly colorless |
| U.S.P. | " | 3 mol % DECA[3] | | 88 | | | |
| 5 | tert.-C$_4$H$_9$— | 0.1 mol % DMF | 50 | 84.3 | 76/67 | — | — |
| Comp. | " | 7 mol % DMF | 50 | 51.4 | | — | — |
| U.S.P. | " | 7 mol % DMF | | 66 | | | |
| 6 | C$_6$H$_5$ | 0.1 mol % DMF | 50 | 92.3 | 106/13 | 97.9 | yellow |
| Comp. | " | 2.7 mol % DMF | 50 | 67.7 | | 94.2 | deep yellow, turbid |
| U.S.P. | " | 13.3 mol % DMF | | 68 | | | |
| 7 | p-CH$_3$—C$_6$H$_4$— | 0.1 Mol % DMF | 50 | 95.2 | 122/13 | 99.2 | yellow |
| Comp. | " | 2.9 Mol % DMF | 50 | 82.6 | | 99.0 | yellow, turbid |

[1]DMF = N,N-dimethyl formamide
[2]TMH = N,N,N',N'-tetramethyl urea
[3]DECA = N,N-diethyl-chloroacetamide

What is claimed is:

1. In a process for the preparation of a thiochloroformate by reacting a mercaptan of the formula

R—SH, in which R is alkyl, cycloalkyl, alkenyl, aryl or aralkyl, or alkyl, cycloalkyl, alkenyl, aryl or aralkyl substituted by one or more substituents selected from the group consisting of halogen radicals, alkoxy radicals, aryloxy radicals, carboalkoxy radicals and SH, with phosgene in the presence of a catalyst, the improvement which comprises reacting said mercaptan with phosgene in the presence of a catalyst selected from the group consisting of carboxylic acid amides, urea derivatives, compounds of the formula

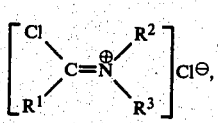

compounds of the formula

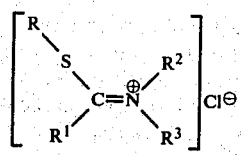

and mixtures of two or more of the foregoing, wherein R is as defined above,
R$^1$ is hydrogen, alkyl, phenyl or

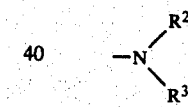

R$^2$ and R$^3$, independently of one another, are hydrogen, alkyl or phenyl, with the proviso that at least one of R$^1$,
R$^2$ and R$^3$ is not hydrogen when R$^1$ is not

and at least one of R$^2$ and R$^3$ is not hydrogen when R$^1$ is

or two of R$^1$, R$^2$ and R$^3$, together, are alkylene, the amount of said catalyst being of from about 0.02 to 0.2 mol percent relative to the amount of the mercaptan.

2. A process as claimed in claim 1, wherein in the mercaptan of the formula

R—SH

R is alkyl of from 1 to 18 carbon atoms or alkyl of from 1 to 18 carbon atoms substituted by one or more substituents selected from the group consisting of halogen radicals, alkoxy radicals, aryloxy radicals, carboalkoxy radicals and the SH group, cycloalkyl of from 5 to 6 carbon atoms or cycloalkyl of from 5 to 6 carbon atoms substituted by one or more substituents selected from the group consisting of halogen radicals, alkoxy radicals, aryloxy radicals, carboalkoxy radicals, alkyl radicals, and the SH group, alkenyl of from 3 to 8 carbon atoms or alkenyl of from 3 to 8 carbon atoms substituted by one or more substituents selected from the group consisting of halogen radicals, alkoxy radicals, aryloxy radicals, carboalkoxy radicals, alkyl radicals, and the SH group, phenyl or phenyl substituted by one or more substituents selected from the group consisting of halogen radicals, alkoxy radicals, aryloxy radicals, carboalkoxy radicals, alkyl radicals, and the SH group, naphthyl or naphthyl substituted by one or more substituents selected from the group consisting of halogen radicals, alkoxy radicals, aryloxy radicals, carboalkoxy radicals, alkyl radicals and the SH group, benzyl or benzyl substituted by one or more substituents selected from the group consisting of halogen radicals, alkoxy radicals, aryloxy radicals, carboalkoxy radicals, alkyl radicals and the SH group, thienyl or thienyl substituted by one or more substituents selected from the group consisting of halogen radicals, alkoxy radicals, aryloxy radicals, carboalkoxy radicals, alkyl radicals and the SH group, or furyl or furyl substituted by one or more substituents selected from the group consisting of halogen radicals, alkoxy radicals, aryloxy radicals, carboalkoxy radicals, alkyl radicals and the SH group.

3. A process as claimed in claim 2, wherein in said mercaptan of the formula

R—SH

R is alkyl of from 1 to 8 carbon atoms or alkyl of from 1 to 8 carbon atoms substituted by one or more substituents selected from the group consisting of halogen radicals, alkoxy radicals, aryloxy radicals, carboalkoxy radicals and the SH group, cycloalkyl of 6 carbon atoms or cycloalkyl of 6 carbon atoms substituted by one or more substituents selected from the group consisting of halogen radicals, alkoxy radicals, aryloxy radicals, carboalkoxy radicals, akyl radicals and the SH group, alkenyl of from 3 to 4 carbon atoms or alkenyl of from 3 to 4 carbon atoms substituted by one or more substituents selected from the group consisting of halogen radicals, alkoxy radicals, aryloxy radicals, carboalkoxy radicals, alkyl radicals and the SH group, or phenyl or phenyl substituted by one or more substituents selected from the group consisting of halogen radicals, alkoxy radicals, aryloxy radicals, carboalkoxy radicals, alkyl radicals and the SH group.

4. The process as claimed in claim 1 or 2, wherein said mercaptan is an alkylmercaptan, said alkyl moiety being of from 1 to 8 carbon atoms, phenylmercaptan or a tolylmercaptan.

5. A process as claimed in claim 1 or 2, wherein said catalyst is a compound of the formula

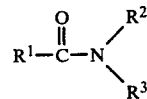

in which $R^1$ is hydrogen, alkyl, phenyl or

$R^2$ and $R^3$, independently of each other, are hydrogen, alkyl or phenyl, with the proviso that at least one of $R^1$, $R^2$ and $R^3$ is not hydrogen when $R^1$ is not

and that at least one of $R^2$ and $R^3$ is not hydrogen when $R^1$ is

or in which two of $R^1$, $R^2$ and $R^3$, together, are alkylene.

6. A process as claimed in claim 5, wherein $R^1$ is alkyl of from 1 to 4 carbon atoms and $R^2$ and $R^3$, independently from one another, are alkyl of from 1 to 4 carbon atoms.

7. A process as claimed in claim 5, wherein two of $R^1$, $R^2$ and $R^3$, together, are alkylene of from 3 to 6 carbon atoms.

8. A process as claimed in claim 1 or 2, wherein said catalyst is dimethyl formamide, tetramethyl urea, N-methylpyrrolidone, or a mixture of two or more of the foregoing.

9. A process as claimed in claim 1 or 2, wherein the amount of said catalyst is of from about 0.05 to about 0.1 mol percent relative to the amount of the mercaptan.

* * * * *